United States Patent
Nichogi et al.

(10) Patent No.: US 8,450,114 B2
(45) Date of Patent: May 28, 2013

(54) METHOD OF STABILIZING CONSTANT-TEMPERATURE PATH

(75) Inventors: Masao Nichogi, Shizuoka (JP); Masao Ushikubo, Shizuoka (JP)

(73) Assignee: Beckman Coulter, Inc., Brea, CA (US)

( * ) Notice: Subject to any disclaimer, the term of this patent is extended or adjusted under 35 U.S.C. 154(b) by 49 days.

(21) Appl. No.: 13/060,263

(22) PCT Filed: Mar. 23, 2009

(86) PCT No.: PCT/JP2009/055606
§ 371 (c)(1),
(2), (4) Date: May 4, 2011

(87) PCT Pub. No.: WO2010/021172
PCT Pub. Date: Feb. 25, 2010

(65) Prior Publication Data
US 2011/0232769 A1    Sep. 29, 2011

(30) Foreign Application Priority Data

Aug. 22, 2008  (JP) ................................. 2008-213806

(51) Int. Cl.
*G01N 35/00* (2006.01)
*G01N 35/10* (2006.01)

(52) U.S. Cl.
USPC .................. 436/49; 422/63; 422/64; 436/43; 436/45

(58) Field of Classification Search
None
See application file for complete search history.

(56) References Cited

U.S. PATENT DOCUMENTS
2005/0135967 A1 *   6/2005   Isobe et al. ................ 422/63

FOREIGN PATENT DOCUMENTS
| JP | 11-201975 | * | 7/1999 |
| JP | 11-201975 | A | 7/1999 |
| JP | 2002-296283 | A | 10/2002 |
| JP | 2008-20311 | * | 1/2008 |
| JP | 2008-20311 | A | 1/2008 |

OTHER PUBLICATIONS

The International Search Report from PCT/JP2009/055606, dated Apr. 28, 2009, included English Translation, 1 page.

* cited by examiner

*Primary Examiner* — P. Kathryn Wright
(74) *Attorney, Agent, or Firm* — Kilpatrick Townsend & Stockton LLP

(57) ABSTRACT

Provided is an automatic analysis apparatus which can obtain stable analysis results by stabilizing a constant-temperature bath and the temperature of a reaction liquid inside reaction containers. For this purpose, the automatic analysis apparatus (1) comprises: a storage tank (10) for storing a temperature controlling liquid (L1) dispensed into reaction containers (5) using dispensing apparatuses (6) and (7); and a dispensation control section for performing a control for dispensing the temperature controlling liquid (L1) using the dispensing apparatuses into an empty reaction container when there is such an empty reaction container, in which neither a specimen nor a reagent is dispensed, on a reaction table (4), where the temperature controlling liquid is cooled down substantially equal to the dispensed reagent by laying a pipe, which is provided between a cooler and a reagent table (2) for passing the coolant, through the temperature controlling liquid in the storage tank.

9 Claims, 7 Drawing Sheets

METHOD OF STABILIZING CONSTANT-TEMPERATURE PATH

CROSS-REFERENCE TO RELATED APPLICATION

This application is a National Stage of International Application No. PCT/JP2009/055606, filed Mar. 23, 2009, which claims the benefit of priority to Japanese Application No. 2008-213806, filed Aug. 22, 2008, the disclosures of each are herein incorporated by reference.

TECHNICAL FIELD

The present invention relates to an automatic analysis apparatus and a method of stabilizing a constant-temperature bath of the automatic analysis apparatus.

BACKGROUND ART

An apparatus for automatically analyzing a specimen, such as blood and body fluids, is conventionally known to dispense a specimen and a reagent into a reaction container to cause a chemical reaction thereof at a predetermined temperature and subsequently optically analyze a reaction liquid. The chemical reaction of the specimen and reagent in the analysis described above takes place in a reaction table having a constant-temperature bath, which is heated close to body temperature, and the temperature control of the constant-temperature bath is extremely important in order to obtain a stable analysis result. As a result, it has been conventional to heat a reagent which is kept cool in a reagent table and subsequently dispense it into a reaction container, and to control the temperature of the constant-temperature bath to be higher than a reaction temperature.

In a case where such an analysis apparatus includes an electrolyte measurement apparatus in addition to biochemical analysis items, a specimen is dispensed into an electrolyte analysis apparatus during electrolyte analysis. Thus, there is a case where there is an empty reaction container among those retained on a reaction table. If there is such an empty reaction container with no reagent or specimen dispensed therein on the reaction table, a reaction temperature of a reaction liquid is likely to change in a reaction container near the empty reaction container. This may result in a lack of accuracy in the analysis results, and therefore, an analysis apparatus is proposed which performs control of dispensing a temperature controlling liquid of a constant-temperature bath into such an empty reaction container (see, for example, Reference 1).

Reference 1: Japanese Laid-Open Publication No. 11-201975

Disclosure of the Invention

The apparatus described in Reference 1 has the following advantage: water is pressurized out of a dispensing apparatus and is dispensed into an empty reaction container, so that air in the reaction container is replaced with the pressurized-out water. This increases the heat capacity on the side where heat is to be controlled, and thereby makes the heat change smaller on the side where heat is to be controlled. The water to be pressurized out is, however, normally at the normal temperature, and a temperature change of a reaction liquid of a specimen and a reagent in a reaction container adjacent to the reaction container, into which the normal temperature pressurized-out water is dispensed, is different from a temperature change of a reaction liquid in a reaction container in the case where a reagent cooled at or below 10 degrees is successively dispensed into reaction containers in the front and back of the reaction container. Thus, there arises a problem of not being able to perform a stable temperature control.

The present invention is intended to solve the problem described above. The objective of the present invention is to provide an automatic analysis apparatus, which steadily dispenses a liquid of a constant temperature into all reaction containers without distinction between a reaction container to be analyzed, into which a specimen and a reagent are dispensed, or a reaction container which is not analyzed, into which the specimen and the reagent are not dispensed, thereby steadily maintaining the amount of heat brought to a reaction table to stabilize a constant-temperature bath and the temperature of a reaction liquid in the reaction containers to obtain a stable analysis result.

An automatic analysis apparatus according to the present invention includes: a reagent table in which a cooling container with a coolant circulating therein keeps a reagent contained inside the cooling container cool; a dispensing apparatus for dispensing a specimen or the reagent into a reaction container; and a reaction table for retaining the reaction container with a liquid dispensed therein, the reaction table heating the reaction container by a constant-temperature bath, the automatic analysis apparatus further including: a storage tank for storing a temperature controlling liquid L1 dispensed into the reaction container using the dispensing apparatus; a storage tank cooling means for cooling the temperature controlling liquid down to substantially a same temperature as the dispensed reagent by laying part of a pipe, which is positioned between a cooler for cooling the coolant and the reagent table and which circulates the coolant, through the temperature controlling liquid in the storage tank; and a dispensation control means for performing a control of dispensing the temperature controlling liquid, using the dispensing apparatus, into an empty reaction container when there is such an empty reaction container, into which neither the specimen nor the reagent is dispensed, on the reaction table, thereby achieving the objective described above.

Further, in the automatic analysis apparatus according to the present invention, the storage tank is provided above a locus of a dispensing probe of the dispensing apparatus.

Still further, in the automatic analysis apparatus according to the present invention, the storage tank includes a dispensation opening for dispensing the temperature controlling liquid using the dispensing apparatus.

Still further, in the automatic analysis apparatus according to the present invention, the storage tank includes: a temperature controlling liquid cooling bath with the storage tank cooling means positioned therein; and a temperature controlling liquid storage bath for storing the temperature controlling liquid cooled in the temperature controlling liquid cooling bath, wherein the temperature controlling liquid storage bath is positioned in a dispensing probe cleaning bath.

Still further, in the automatic analysis apparatus according to the present invention, the dispensation control means performs a control of dispensing the cooled temperature controlling liquid, using the dispensing apparatus, into the empty reaction container before a start of an analysis and after an end of the analysis.

Still further, in the automatic analysis apparatus according to the present invention, the dispensation control means dispenses the cooled temperature controlling liquid into the empty reaction container at the timing of dispensing a first reagent.

Still further, in the automatic analysis apparatus according to the present invention, the dispensation control means controls to dispense an average amount of the reagent and the specimen dispensed in each analysis item as a dispensing amount of the temperature controlling liquid.

Still further, in the automatic analysis apparatus according to the present invention, the constant-temperature bath in the reaction table uses a dry bath method.

A method of stabilizing a constant-temperature bath of an automatic analysis apparatus according to the present invention includes: a reagent table in which a cooling container with a coolant circulating therein keeps a reagent contained inside the cooling container cool; a dispensing apparatus for dispensing a specimen or the reagent into a reaction container; and a reaction table for retaining the reaction container with a liquid dispensed therein, the reaction table heating the reaction container by a constant-temperature bath, the method including: a cooling step of cooling a temperature controlling liquid in a storage tank including a pipe laid therein for passing the coolant between a cooler, which cools the coolant for keeping inside the reagent table cool, and the reagent table; and a dispensing step of dispensing the cooled temperature controlling liquid using the dispensing apparatus into an empty reaction container, in which neither the specimen not the reagent is dispensed, on the reaction table.

Further, in the method of stabilizing a constant-temperature bath of an automatic analysis apparatus according to the present invention, in the dispensing step, the cooled temperature controlling liquid is dispensed into the empty reaction container at the timing of dispensing a first reagent.

Still further, in the method of stabilizing a constant-temperature bath of an automatic analysis apparatus according to the present invention, in the dispensing step, a dispensing amount of the temperature controlling liquid is defined as an average amount of the reagent and the specimen dispensed in each analysis item.

The automatic analysis apparatus according to the present invention cools a temperature controlling liquid down to substantially the same temperature as a dispensed reagent by laying a part of a pipe, which is placed between a cooler and a reagent table for passing a coolant, through the temperature controlling liquid in a storage tank, and when there is an empty reaction container, in which neither a specimen nor a reagent is dispensed, on a reaction table, the automatic analysis apparatus dispenses the temperature controlling liquid into the empty reaction container using a dispensing apparatus. As a result, it becomes possible to dispense a liquid of a constant temperature steadily into all the reaction containers to create a temperature change condition similar to the successive dispensation, and steadily maintain the amount of heat brought into the reaction table at all times. Thereby, the constant-temperature bath and the temperature of the reaction liquid in the reaction containers can be stabilized to attain an effect of obtaining a stable analysis result.

Figure 1:
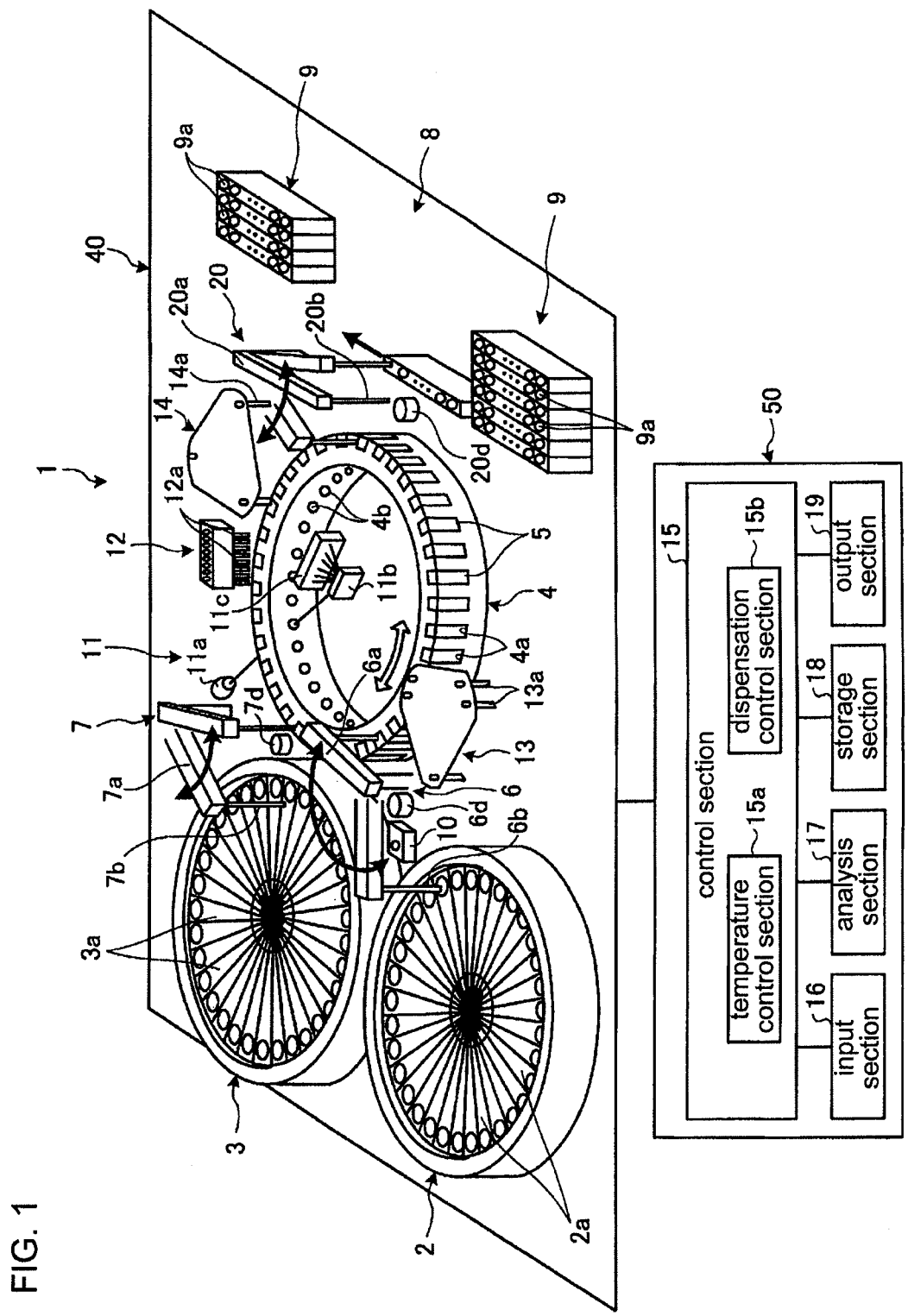
FIG. 1 is a schematic structural diagram of an automatic analysis apparatus according to Embodiment 1 of the present invention.

1 automatic analysis apparatus
2, 3 first and second reagent tables
2a, 3a reagent container
2b temperature sensor
2c coolant pipe
2d cooler
4 reaction table
4a hold section
4b optical path
41 lid section
42 rotation table
43 main body section
44 constant-temperature bath
45 rotation table driving apparatus
46 rubber heater
5 reaction container
6, 7 first and second reagent dispensing apparatuses
6a driving arm
6b dispensing probe
6c support
6d, 6d' cleaning bath
6e pipe
6f wheel
8 specimen container transferring mechanism
9 rack
9a specimen container
10, 10B temperature controlling liquid storage tank
100B temperature controlling liquid cooling bath
101B temperature controlling liquid storage bath
10a dispensation opening
11 analytical optical system
12 cleaning mechanism
13, 14 first and second stirring apparatuses
15 control section
15a temperature control section
15b dispensing control section
16 input section
17 analysis section
18 storage section
19 output section
20 specimen dispensing apparatus
31 liquid level detecting mechanism
40 measurement mechanism
50 control mechanism
60 probe driving mechanism
61 pivoting motor
61a revolving shaft
61b, 62c wheel
61c, 62a timing belt
62 ascending and descending motor
62b screw shaft
62d ascending and descending block
63a cleaning bath
63b nozzle section
63c, 63h pipe
63d, 63g electromagnetic valve
63e cleaning water tank 63f disposal tank
63i pump
L1 temperature controlling liquid

BEST MODE FOR CARRYING OUT THE
INVENTION

Hereinafter, an automatic analysis apparatus and a method of stabilizing a constant-temperature bath will be described, which is the best mode for carrying out the present invention. It should be noted that the present invention is not limited to the following embodiments, and that identical portions or corresponding portions are given the same reference numerals in the description of the figures.

(Embodiment 1)

FIG. 1 is a schematic structural diagram of an automatic analysis apparatus according to Embodiment 1 of the present invention. As illustrated in FIG. 1, an automatic analysis apparatus 1 includes: a measurement mechanism 40 for dispensing a specimen and a reagent into a reaction container 5 to optically measure a reaction caused in the dispensed reaction container 5; and a control mechanism 50 for performing control of the entire automatic analysis apparatus 1 including the measurement mechanism 40 and performing an analysis of a measurement result in the measurement mechanism 40. The automatic analysis apparatus 1 automatically performs a biochemical, immunological or genetical analysis of a plurality of specimens with the cooperation of the two mechanisms.

The measurement mechanism 40 broadly includes: first and second reagent tables 2 and 3; a reaction table 4; first and second reagent dispensing apparatuses 6 and 7; a specimen container transferring mechanism 8; a rack 9; an analytical optical system 11; a cleaning mechanism 12; first and second stirring apparatuses 13 and 14; a specimen dispensing apparatus 20; and a temperature controlling liquid storage tank 10. Each of these sections included in the measurement mechanism 40 and control mechanism 50 is electrically connected to a control section 15.

As illustrated in FIG. 1, in the first and second reagent tables 2 and 3, a plurality of reagent containers 2a for a first reagent and a plurality of reagent containers 3a for a second reagent are arranged respectively in a circular direction, where the first and second reagent tables 2 and 3 are rotated by a driving means to convey the reagent containers 2a and 3a in a circular direction. The plurality of reagent containers 2a and 3a each are filled with a reagent in accordance with a test item, and an information recording medium (not shown) is attached to an external surface of the reagent containers, and the medium records information on the type of a contained reagent, a lot, a term of validity and the like. On each outer circumference of the first and second reagent tables 2 and 3, a reading apparatus (not shown) is provided for reading and outputting the reagent information recorded on the information recording medium, which is added to the reagent containers 2a and 3a, to the control section 15.

As illustrated in FIG. 1, a plurality of reaction containers 5 are arranged in the reaction table 4 along the circular direction thereof. The reaction table 4 is rotated in a direction indicated by the arrow to move the reaction containers 5 in a circular direction by a driving means, which is different from the driving means for driving the first and second reagent tables 2 and 3. The reaction table 4 is placed in between a light source 11a and a spectral section 11b, and includes: a hold section 4a for holding the reaction container 5; and an optical path 4b consisting of a circular opening for guiding a beam output from the light source 11a to the spectral section 11b. Each hold section 4a is arranged at a predetermined interval on the outer circumference of the reaction table 4 along the circular direction, and the optical path 4b is formed, extending in a radial direction, on the internal circumference side of the hold section 4a.

Figure 2:
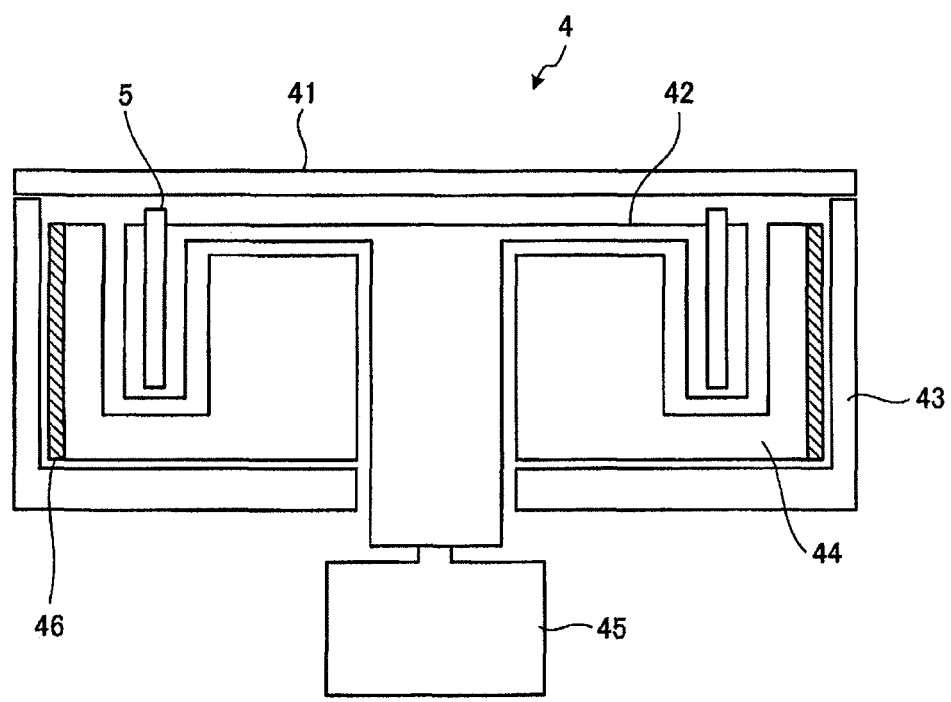
FIG. 2 is a cross sectional view of a reaction table used in the automatic analysis apparatus in FIG. 1.

FIG. 2 is a cross sectional view of the reaction table 4. The reaction table 4 includes: a main body section 43, which is a cylindrical shape with an open top; and a freely opened/closed, lid section 41 for covering the opening to control temperature change in a constant-temperature bath 44. The main body section 43 forms a bottom surface and a side surface of the reaction table 4, and includes therein, the constant-temperature bath 44 for performing a reaction of a specimen and a reagent. A rotation table 42 is provided above the constant-temperature bath 44, and the rotation table 42 is connected to a rotation table driving apparatus 45 so that the rotation table 42 pivots clockwise or counterclockwise, by the driving of the rotation table driving apparatus 45, with a vertical line along the center of the rotation table 42 as the axis of rotation. The outer circumference of the constant-temperature bath 44 below the rotation table 42 is surrounded by a rubber heater 46, and the constant-temperature bath 44 is heated by the rubber heater 46 to a temperature around a body temperature, which is the temperature at which a reaction is performed. For the constant-temperature bath 44, exemplary baths are: a constant-temperature bath with a wet bath method which uses a constant-temperature liquid, such as water, as a heat medium, and a constant-temperature bath with a dry bath method which uses a solid-body, such as metal, as a heat medium with an interposed air layer as a clearance section. In Embodiment 1, a constant-temperature bath with a dry bath method is preferably used, which has excellent maintainability but has a low heat exchange rate.

The reaction container 5 is a container called a cuvette, which is molded in a quadrilateral cylinder shape with an optically transparent material which transmits 80% or more of light contained in analytical light (340 nm to 800 nm) output from the analytical optical system 11. The optically transparent material includes, for example, glass including heat-resistant glass, ring-shaped olefin, polystyrene and the like. A reagent is dispensed into the reaction container 5 from the reagent containers 2a and 3a of the first and second reagent tables 2 and 3 by the first and second reagent dispensing apparatuses 6 and 7 provided near the reaction container 5. The first and second reagent dispensing apparatuses 6 and 7 respectively include arms 6a and 7a each pivoting on a horizontal plane and ascending and descending in upper and lower directions, with dispensing probes 6b and 7b provided thereto for dispensing a reagent.

As illustrated in FIG. 1, the specimen container transferring mechanism 8 transfers a plurality of arranged racks 9 along the arrow direction one container at a time. Each rack 9 retains a plurality of specimen containers 9a containing a specimen. A bar code or the like for recording information of contained specimen is adhered to the specimen container 9a, and the specimen is dispensed into each reaction container 5 by the specimen dispensing apparatus 20 every time the incremental step of the racks 9 transferred by the specimen container transferring mechanism 8 stops. The specimen dispensing apparatus 20 includes an arm 20a pivoting a horizontal plane and ascending and descending in upper and lower directions, with a dispensing probe 20b provided thereto for dispensing a reagent. On the outer circumference of the rack, a reading apparatus (not shown) is provided for reading and outputting specimen information, which is recorded on the information recording medium (not shown) adhered to the specimen container 9a, and container information of the specimen container 9a, to the control section 15.

The analytical optical system 11 is an optical system for transmitting to a liquid sample in a reaction container 5, in which a reagent and a specimen have reacted with each other and analyzing analytical light (340 nm to 800 nm). The analytical optical system 11 includes a light source 11a, a spectral section 11b, and a light receiving section 11c. The analytical light output from the light source 11a passes through the liquid sample in the reaction container 5 and is received by the light receiving section 11c provided at a position facing the spectral section lib. The light receiving section 11c is connected to the control section 15.

The cleaning mechanism 12 sucks and discharges the liquid sample in the reaction container 5 by a nozzle 12a. Subsequently, the cleaning mechanism 12 repeatedly injects and sucks a cleaning liquid, such as a cleaner or a cleaning water, by the nozzle 12a to clean the reaction container 5, for which analysis has been completed by the analytical optical system 11.

The first and second stirring apparatuses 13 and 14 each stir a specimen and a reagent dispensed into reaction containers 5, using stirring rods 13a and 14a to promote the reaction.

Figure 3:
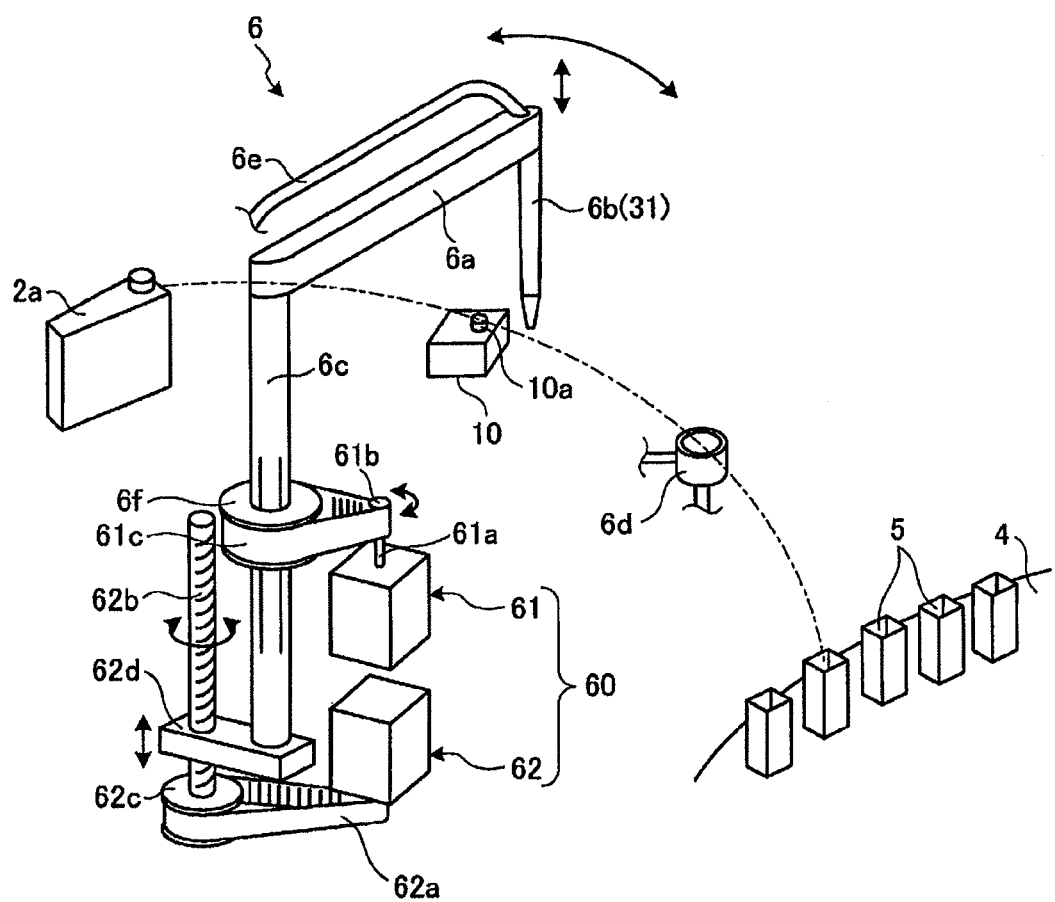
FIG. 3 is a schematic structural diagram of a first reagent dispensing apparatus used in the automatic analysis apparatus in FIG. 1.

FIG. 3 is a schematic structural diagram of a first reagent dispensing apparatus 6. The first reagent dispensing apparatus 6 and the second reagent dispensing apparatus 7 have identical structures, and therefore, the first reagent dispensing apparatus 6 will be described as a representative example.

The first reagent dispensing apparatus 6 includes: a probe driving mechanism 60; and an electrostatic capacitance type liquid level detecting mechanism 31. As illustrated in FIGS. 1 and 2, the first reagent dispensing apparatus 6 further includes: a driving arm 6a for pivoting in a horizontal direction between a reagent container 2a and a reaction container 5 and for ascending and descending in upper and lower directions; a dispensing probe 6b supported by the driving arm 6a; a support 6c for supporting the driving arm 6a; and a cleaning bath 6d for cleaning the dispensing probe 6b. The dispensing probe 6b dispenses a first reagent, and is a probe which is a structural element of the liquid level detecting mechanism 31. For example, the dispensing probe 6b is molded with a conductive material, such as aluminum. The dispensing probe 6b discharges a sucked first reagent into a reaction container 5, and subsequently discharges cleaning water supplied from a pipe 6e into the cleaning bath 6d, so that the interior of the dispensing probe 6b is cleaned. The cleaning bath 6d is connected to a pipe for ejecting cleaning water into the tank and a pipe for discharging the cleaning water, which has been ejected into the tank to clean the outer surface of the dispensing probe 6b. The cleaning bath 6d is placed over a movement locus of the dispensing probe 6b.

The probe driving mechanism 60 ascends and descends as well as pivots the dispensing probe 6b, and includes a pivoting motor 61 and an ascending and descending motor 62, as illustrated in FIG. 3. The pivoting motor 61 includes a timing belt 61c wrapped around a wheel 61b attached to a revolving shaft 61a and a wheel 6f attached to the support 6c. The ascending and descending motor 62 rotates a screw shaft 62b through a timing belt 62a to move an ascending and descending block 62d vertically along the screw shaft 62b. The timing belt 62a is wrapped around a wheel attached to a revolting shaft and a wheel 62c attached to a lower end of the screw shaft 62b. The ascending and descending block 62d is attached to the lower end of a support 6c to support the support 6c, and constitutes a ball screw together with the screw shaft 62b.

The liquid level detecting mechanism 31 is a means for detecting a liquid level of a reagent in a reagent container 2a, and detects an electrostatic capacitance between an electrode (not shown), which is provided integrally with or near the reagent container 2a, and a dispensing probe 6b, and detects a liquid level by the change in an electrostatic capacitance at the time when the dispensing probe 6b contacts the reagent.

In the meantime, as illustrated in FIG. 3, the temperature controlling liquid storage tank 10 is placed over a pivoting trajectory in a horizontal plane of the dispensing probe 6b. The temperature controlling liquid storage tank 10 is a tank for storing a temperature controlling liquid L1, which is cooled down to the same temperature as the reagent in the reagent table 2. The temperature controlling liquid L1 in the temperature controlling liquid storage tank 10 is sucked through a dispensation opening 10a by the first reagent dispensing apparatus 6, and the sucked temperature controlling liquid L1 is dispensed into an empty reaction container 5 on the reaction table 4 to stabilize a constant temperature performance of the constant-temperature bath in the reaction table 4. The probe driving mechanism 60 transfers the dispensing probe 6b over the temperature controlling liquid storage tank 10 by the driving arm 6a, and subsequently, inserts the dispensing probe 6b into the temperature controlling liquid storage tank 10. The temperature controlling liquid L1 is sucked by the dispensing probe 6b with suction pressure of a syringe pump (not shown) connected to the pipe 6e. The temperature controlling liquid L1 is transferred over the reaction table 4 by the driving arm 6a, and is subsequently discharged into the reaction container 5 into which neither a reagent nor a specimen is dispensed.

Figure 4:
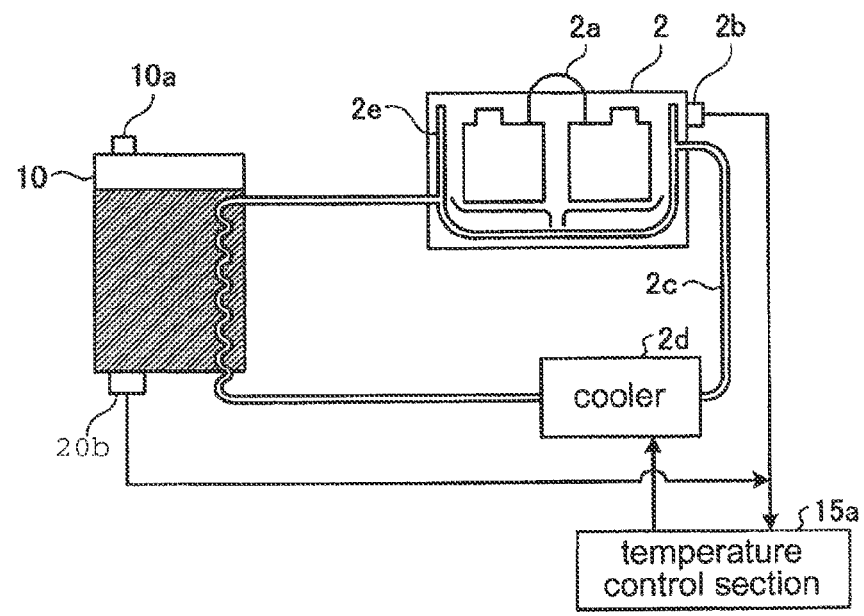
FIG. 4 is a block diagram schematically illustrating a temperature controlling system with a temperature controlling liquid storage tank of the automatic analysis apparatus in FIG. 1 as the central figure.

With reference to a block diagram schematically illustrating a temperature controlling system with the temperature controlling liquid storage tank 10 of the automatic analysis apparatus 1 as the central figure in FIG. 4, the temperature controlling liquid storage tank 10 will be described. As illustrated in FIG. 4, temperature sensors 2b and 20b are provided for the reagent table 2 and the temperature controlling liquid storage tank 10 respectively, and temperature information from the temperature sensors 20b is managed and controlled by a temperature control section 15a. The temperature of the reagent table 2 and the temperature controlling liquid storage tank 10 is adjusted to about 4° C. to 12° C. to prevent the reagent from being degenerated or stripped. The reagent table 2 circulates a coolant, which is cooled down by a cooler 2d, through a coolant pipe 2c to a cooling container 2e in the reagent table 2 by a pump (not shown) for keeping the reagent table 2 cool. The coolant passes from the coolant pipe 2c through the cooling container 2e in the reagent table 2 and goes into the temperature controlling liquid storage tank 10. Subsequently, the coolant goes into the cooler 2d. After the coolant is cooled down to a set temperature, it again passes through the coolant pipe 2c. The temperature controlling liquid L1 stored in the temperature controlling liquid storage tank 10 is cooled down equal to the temperature of the reagent by laying the coolant pipe 2c, through which the coolant for keeping inside the reagent table 2 cooled passes, through the temperature controlling liquid storage tank 10. Distilled water or degassed water is used as the temperature controlling liquid L1.

Next, the control mechanism 50 will be described. The control mechanism 50 includes: a control section 15; an input section 16; an analysis section 17; a storage section 18; and an output section 19. The control section 15 is connected to each of the sections included in the measurement mechanism 40 and the control mechanism 50. A microcomputer or the like is used in the control section 15 to control the operation of the sections. The control section 15 performs a predetermined input and output control on information input to and output from these constituent parts, and also performs predetermined information processing on the information. The control section 15 also includes: a temperature control section 15a; and a dispensing control section 15b. The temperature control section 15a performs a temperature control of the reagent table 2 and inside the temperature controlling liquid storage tank 10. The dispensing control section 15b performs switching between a normal dispensing mode and a special dispensing mode. The normal dispensing mode is a reagent dispensing mode in a case where a specimen and a reagent are dispensed into reaction containers 5 to perform an analysis at the reaction table 4 by the analytical optical system 11. Also, the special dispensing mode is a mode for dispensing the temperature controlling liquid L1, instead of a specimen and a reagent, into the reaction containers 5, in such cases where a specimen container or a reagent container is replaced, where an analysis item is an electrolyte, and further where there is a residual liquid due to incomplete cleaning of a reaction container. In addition, at a start-up or cooling-down of the automatic analysis apparatus 1, the temperature controlling liquid L1 is controlled to be dispensed into the reaction container 5 through the special dispensing mode.

The input section 16 is constituted of a keyboard, a mouse and the like, and obtains various kinds of information necessary for the analysis of a specimen and instruction information for analysis operations, from the outside. The analysis section 17 calculates absorbance and the like based on a measurement result obtained from the analytical optical system 11 to perform component analysis of a specimen or the like. The storage section 18 is constituted of: a hard disk for magnetically storing information; and a memory for loading and electrically storing various programs from the hard disk, the programs being related to the processing by the automatic analysis apparatus 1. The storage section 18 stores various kinds of information including an analysis result of a specimen and the like. The storage section 18 may include an auxiliary storage apparatus capable of reading information stored in a recording medium, such as a CD-ROM, a DVD-ROM, a PC card or the like. The output section 19 is constituted of a printer, a communication mechanism and the like, and outputs various kinds of information including an analysis result of a specimen.

In the automatic analysis apparatus 1 with the structure described above, the first reagent dispensing apparatus 6 dispenses a first reagent in the reagent container 2a, and subsequently the specimen dispensing apparatus 20 dispenses a specimen in the specimen container 9a, into the plurality of reaction containers 5 which are successively conveyed in line. Further, the second reagent dispensing apparatus 7 dispenses a second reagent in the reagent container 3a thereinto, and the analytical optical system 11 performs spectral intensity measurement of a sample obtained by the reaction of a specimen and a reagent. The measurement result is analyzed by the analysis section 17. As a result, the component analysis of the specimen and the like can be performed automatically. In addition, the cleaning mechanism 12 cleans the reaction containers 5, which are conveyed after the measurement by the analytical optical system 11, while conveying them, so that a series of analysis operations can be repeatedly performed successively.

Figure 5:
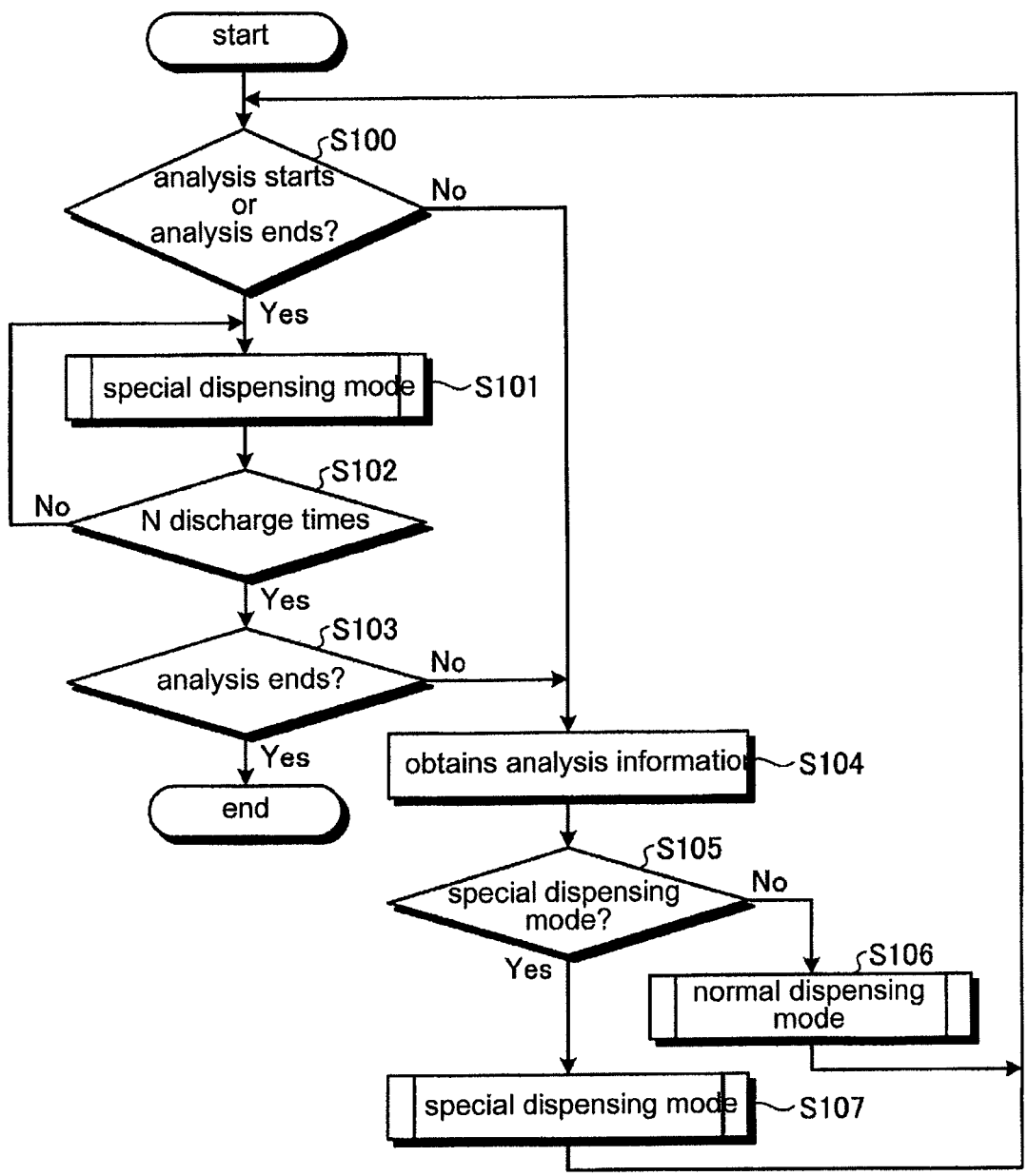
FIG. 5 is a flowchart illustrating a dispensing operation of a temperature controlling liquid according to Embodiment 1 of the present invention.
Figure 6:
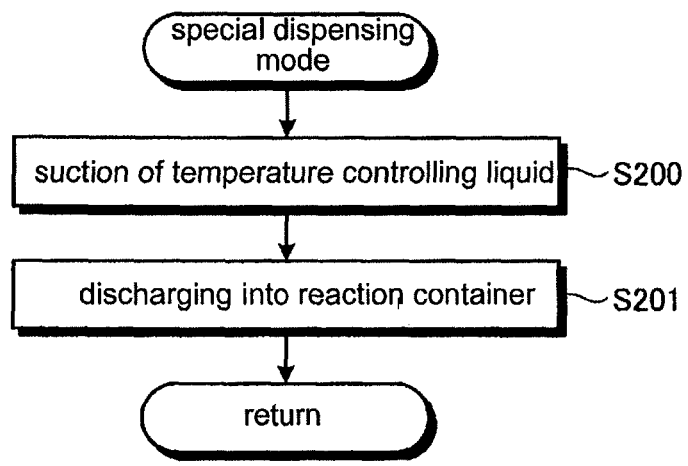
FIG. 6 is a flowchart illustrating a dispensing operation of a special dispensing mode.
Figure 7:
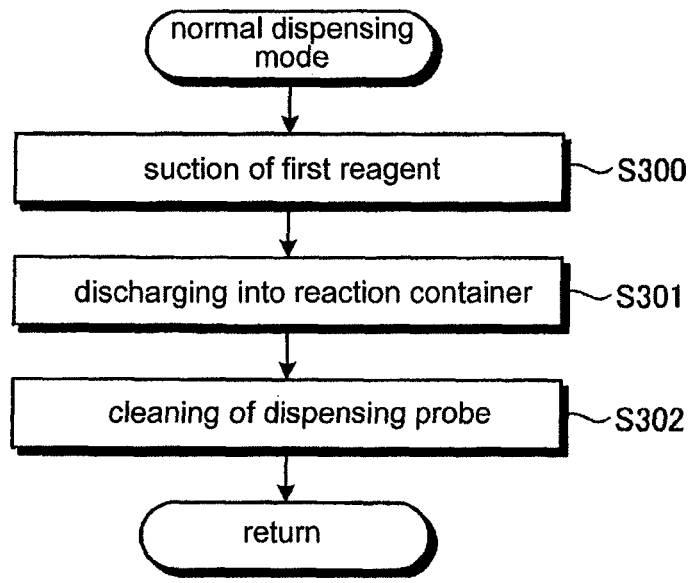
FIG. 7 is a flowchart illustrating a dispensing operation of a normal dispensing mode.

Next, dispensing operations for the temperature controlling liquid L1 will be described. FIG. 5 is a flowchart illustrating a dispensing operation of a temperature controlling liquid L1. In addition, FIG. 6 is a flowchart illustrating a dispensing operation in a special dispensing mode. In addition, FIG. 7 is a flowchart illustrating a normal dispensing mode.

With reference to FIG. 5, an overall flow will be described with regard to a dispensing operation for the temperature controlling liquid L1. The dispensing control section 15b confirms whether or not the state of the automatic analysis apparatus 1 is in an analysis starting time or in an analysis ending time (step S100). In the case where the state is in an analysis starting time or in an analysis ending time (step S100, Yes), a special dispensing mode is switched on in order to stabilize the constant temperature performance of the constant-temperature bath in the reaction table 4 (step S101). In the special dispensing mode illustrated in FIG. 6, the first reagent dispensing apparatus 6 is used to suck the temperature controlling liquid L1 in the temperature controlling liquid storage tank 10, which liquid is cooled down as low as the temperature of a reagent in the reagent table 2 (step S200), and the temperature controlling liquid L1 is discharged into the reaction container 5 (step S201). In the special dispensing mode, the temperature controlling liquid L1 is cooled distilled water or degassed water, and therefore, it is not necessary to clean the dispensing probe 6b. The dispensing amount of the temperature controlling liquid L1 in this case is the average of a total amount of the first reagent, specimen and second reagent dispensed into the reaction container 5. In addition, by dispensing the temperature controlling liquid L1, which is cooled down to the same temperature as the first reagent, into the reaction container 5 immediately before the start of the analysis, it becomes easy to control the reaction temperature in the reaction container 5 into which a specimen and a reagent are dispensed upon starting the analysis. In addition, in a case where the temperature controlling liquid L1 is dispensed into a reaction container 5 immediately after another reaction container 5 into which a specimen and a reagent are dispensed lastly by the end of an analysis, the controlling of a reaction temperature becomes easy in the immediately prior reaction container 5 into which the specimen and the reagent are dispensed.

The dispensing of the temperature controlling liquid L1 into an empty reaction container 5 at the analysis starting time or the analysis ending time is performed by designating the number of times (N times) as one or more times, and preferably five times or more, to stabilize the constant temperature performance of the constant-temperature bath. If the number of dispensing times of the temperature controlling liquid L1 is less than the N times (step S102, No), the special dispensing mode (step S101) is performed until the number becomes N times. If the number of dispensing times for the temperature controlling liquid L1 becomes N times (step S102, Yes), it is confirmed whether the analysis ends (step S103). If the analysis has not ended (step S103, No), analysis information is obtained from the storage section 18 to start the analysis at a step S104. After the analysis information is obtained (step S104), it is confirmed as to whether the dispensing by the first reagent dispensing apparatus 6 is in the special dispensing mode or not (step S105). In the case of the normal dispensing mode (step 5105, No), as illustrated in FIG. 7, the first reagent on the first reagent table 2 is sucked by the first reagent dispensing apparatus 6 (step S300), the first reagent is discharged into the reaction container 5 (step S301), and the dispensing probe 6b of the first reagent dispensing apparatus 6 is cleaned in the cleaning bath 6d (step S302). After the ending of the normal dispensing mode at the step S106, the steps S100 to S105 are repeated to perform new dispensing. In a case of the special dispensing mode (step 5105, Yes), the dispensing probe 6b sucks the cooled temperature controlling liquid L1 and discharges the temperature controlling liquid L1 into the reaction container 5 (step S107), and subsequently, the steps S100 to S105 are repeated.

If all analysis items have ended (step S100, Yes), the steps S101 to S102 are repeated in order to obtain a stable analysis result of a reaction liquid dispensed into a reaction container 5 immediately prior to the end of the analysis. After the special dispensing mode is performed successively for N times (step S102, Yes), the analysis is ended (step S103, Yes). At the starting of the analysis and the ending of the analysis, as well as during a successive operation of the automatic analysis apparatus 1, the temperature controlling liquid L1 which is cooled down to the same temperature as the reagent as described above is dispensed into an empty reaction container 5 into which neither of a reagent nor a specimen is dispensed. As a result, the amount of heat brought into the constant-temperature bath 44 in the reaction table 4 by the dispensing of a reagent and a specimen or by the dispensing of the temperature controlling liquid L1 becomes substantially equal, and it becomes possible to obtain a stable analysis result by the stabilization of the constant temperature performance of the constant-temperature bath 44. Further, in Embodiment 1, the temperature controlling liquid L1 stored in the temperature controlling liquid storage tank 10 is cooled down by laying part of the coolant pipe 2c, which is placed between the cooler 2d for cooling down the coolant and the reagent table 2 and through which the coolant passes, through the temperature controlling liquid storage tank 10. Thereby, the installment space and cost can be reduced.

In Embodiment 1, the timing of dispensing the temperature controlling liquid L1 into the reaction container 5 is determined to be a first reagent dispensing time at which the dispensing amount is the most, and the temperature controlling liquid L1 is dispensed by the first reagent dispensing apparatus 6. In the case where a more accurate control is performed for the reaction temperature, the following may be performed: at the time of dispensing the first reagent, the cooled temperature controlling liquid L1 of the average dispensing amount of the first reagent is dispensed by the first reagent dispensing apparatus 6 into the reaction container 5; at the time of dispensing the specimen, probe cleaning water (pressurized-out water) at the normal temperature and of the average dispensing amount of the specimen is dispensed from the specimen dispensing apparatus 20 into the reaction container 5; and at the time of dispensing the second reagent, the cooled temperature controlling liquid L1 of the average dispensing amount of the second reagent is dispensed by the second reagent dispensing apparatus 7 into the reaction container 5.

(Embodiment 2)

A temperature controlling liquid storage tank 10B according to Embodiment 2 includes: a temperature controlling liquid cooling bath 100B provided with a coolant pipe 2c functioning as a storage tank cooling means; and a temperature controlling liquid storage bath 101B for storing cooled temperature controlling liquid. The temperature controlling liquid storage bath 101B is placed in a cleaning bath 6d', independent from the temperature controlling liquid cooling bath 100B.

Figure 8:
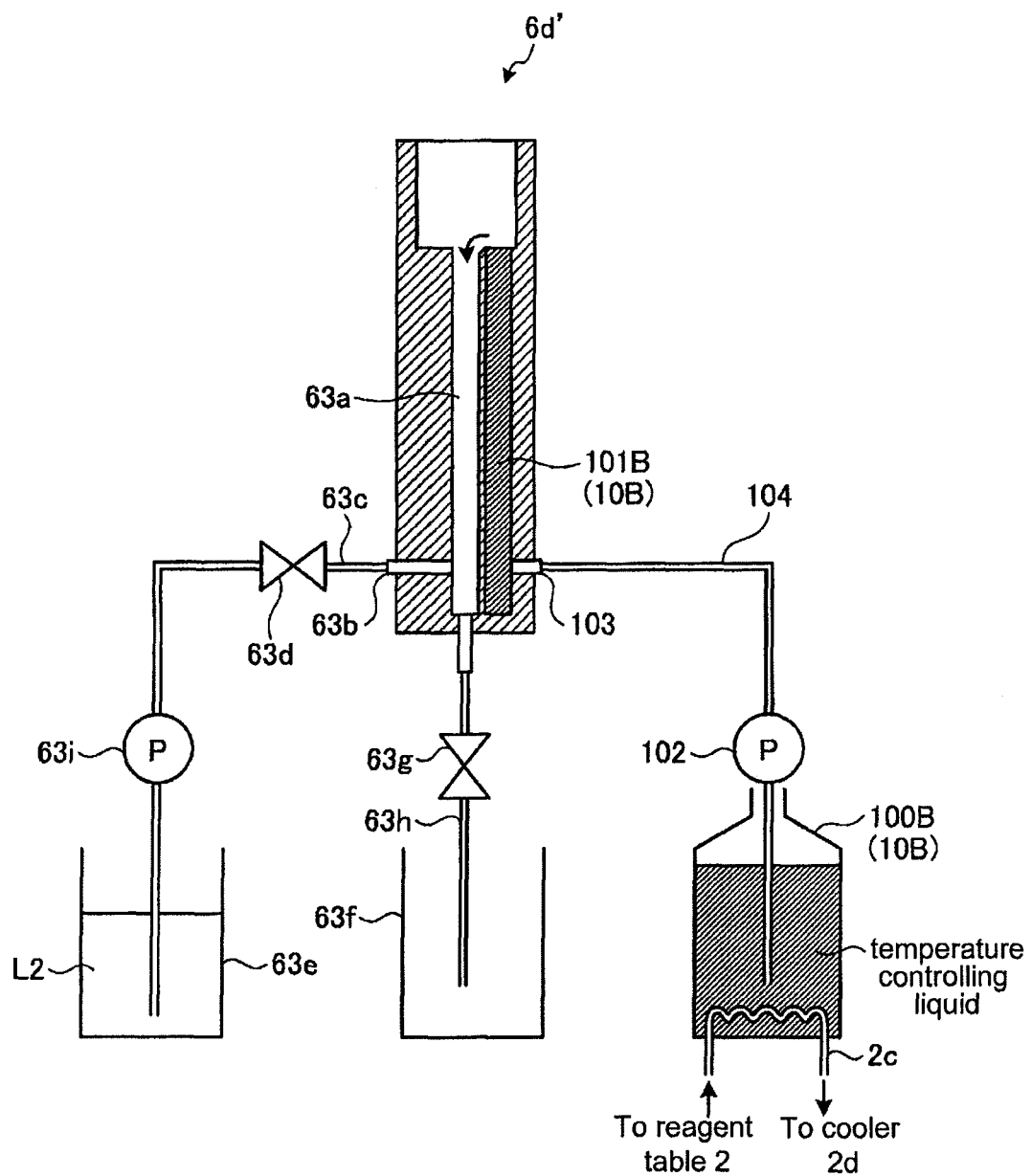
FIG. 8 is a schematic structural diagram of a dispensing probe cleaning bath according to Embodiment 2 of the present invention.

With reference to a schematic structural diagram of the cleaning bath 6d' in FIG. 8, the temperature controlling liquid storage tank 10B will be described. As illustrated in FIG. 8, the temperature controlling liquid cooling bath 100B and the temperature controlling liquid storage bath 101B of the temperature controlling liquid storage tank 10B are independently provided, and the temperature controlling liquid storage bath 101B is placed inside the cleaning bath 6d'. In the temperature controlling liquid cooling bath 100B, a coolant pipe 2c is placed, which is connected to a cooler 2d and a reagent table 2. The coolant pipe 2c in the temperature controlling liquid cooling bath 100B connects the cooler 2d and the reagent table 2, and a coolant which is cooled down in the cooler 2d passes through the coolant pipe 2c. The coolant cooled down by the cooler 2d passes through the coolant pipe 2c, so that a temperature controlling liquid L1 inside the temperature controlling liquid cooling bath 100B is cooled down. The temperature controlling liquid cooling bath 100B and the temperature controlling liquid storage bath 101B are connected by a pipe 104 with a pump 102 interposed therebetween, and the cooled temperature controlling liquid L1 is supplied from a nozzle section 103 provided in the lower part of the temperature controlling liquid storage bath 101B. The temperature controlling liquid L1 supplied from the nozzle section 103 is stored in the temperature controlling liquid storage bath 101B and a dispensing probe 6b is descended into the temperature controlling liquid storage bath 101B to suck the temperature controlling liquid L1.

The temperature controlling liquid L1 in the temperature controlling liquid storage bath 101B may be overflowed from the top part of the storage bath to an adjacent cleaning bath 63a, and the overflowed temperature controlling liquid L1 is either disposed of through a pipe 63h into a disposal tank 63f by opening an electromagnetic valve 63g, or stored in a cleaning bath 63a by closing the electromagnetic valve 63g. When the dispensing probe 6b is cleaned after reagent dispensing, an electromagnetic valve 63d is opened, and cleaning water L2 in a cleaning water tank 63e is supplied from a nozzle section 63b through a pipe 63c into the cleaning bath 63a by the driving of a pump 63i, and the cleaning water L2 is stored into the cleaning bath 63a.

In Embodiment 2, the temperature controlling liquid storage tank 10B includes the temperature controlling liquid cooling bath 100B and the temperature controlling liquid storage bath 101B, and the temperature controlling liquid storage bath 101B is provided inside the cleaning bath 6d'. As a result, the position for providing the temperature controlling liquid cooling bath 100B can be freely adjusted to some degree, and the size of the temperature controlling liquid cooling bath 100B can be relatively large without the limitation of the installation site.

The present invention may also include various other embodiments not described herein, and various design modifications and the like can be made without departing from the scope of the technical ideas specified by the claims.

INDUSTRIAL APPLICABILITY

As described above, the automatic analysis apparatus and the method for stabilizing a constant-temperature bath according to the present invention are suitable for an automatic analysis apparatus for optically measuring a reactant of a specimen and a reagent to analyze components of the specimen, and in particular, suitable for an analysis in which high analytic accuracy is required.

The invention claimed is:

1. An automatic analysis apparatus comprising: a reagent table in which a cooling container with a coolant circulating therein keeps a reagent contained inside the cooling container cool; a dispensing apparatus for dispensing a specimen or the reagent into a reaction container; a reaction table for retaining the reaction container with a liquid dispensed therein, the reaction table heating the reaction container by a constant-temperature bath; and an analytical optical system for measuring reaction contents in the reaction container, the automatic analysis apparatus further comprising:

a storage tank for storing a temperature controlling liquid L1 dispensed into the reaction container using the dispensing apparatus;

a storage tank cooling means for cooling the temperature controlling liquid down to substantially a same temperature as the dispensed reagent wherein part of a pipe, which is positioned between a cooler for cooling the coolant and the reagent table and which circulates the coolant, is located within the temperature controlling liquid in the storage tank; and a dispensation control means for performing a control of dispensing the temperature controlling liquid, using the dispensing apparatus, into an empty reaction container when there is such an empty reaction container, into which neither the specimen nor the reagent is dispensed, on the reaction table;

wherein the storage tank includes: a temperature controlling liquid cooling bath with the storage tank cooling means positioned therein; and a temperature controlling liquid storage bath for storing the temperature controlling liquid cooled in, and provided by, the temperature controlling liquid cooling bath, wherein the temperature controlling liquid storage bath includes a dispensation opening for dispensing the temperature controlling liquid using the dispensing apparatus.

2. The automatic analysis apparatus according to claim 1, wherein the storage tank is provided on a pivoting trajectory of a dispensing probe of the dispensing apparatus.

3. The automatic analysis apparatus according to claim 1, wherein the dispensation control means performs a control of dispensing the cooled temperature controlling liquid, using the dispensing apparatus, into the empty reaction container before a start of an analysis and after an end of the analysis.

4. The automatic analysis apparatus according to claim 1, wherein the dispensation control means dispenses the cooled temperature controlling liquid into the empty reaction container at the timing of dispensing a first reagent.

5. The automatic analysis apparatus according to claim 1, wherein the dispensation control means controls to dispense an average amount of the reagent and the specimen dispensed in each analysis item as a dispensing amount of the temperature controlling liquid.

6. The automatic analysis apparatus according to claim 1, wherein the constant-temperature bath in the reaction table comprises a solid-body as a heat medium and an air layer as a clearance section.

7. A method of stabilizing a constant-temperature bath of an automatic analysis apparatus comprising: a reagent table in which a cooling container with a coolant circulating therein keeps a reagent contained inside the cooling container cool;

a dispensing apparatus for dispensing a specimen or the reagent into a reaction container; a reaction table for retaining the reaction container with a liquid dispensed therein, the reaction table heating the reaction container by a constant-temperature bath; and an analytical optical system for measuring reaction contents in the reaction container, the method comprising:

a cooling step of cooling a temperature controlling liquid in a storage tank including a pipe laid therein for passing the coolant between a cooler, which cools the coolant for keeping inside the reagent table cool, and the reagent table; and a dispensing step of dispensing the cooled temperature controlling liquid using the dispensing apparatus into an empty reaction container, in which neither the specimen not the reagent is dispensed, on the reaction table;

wherein the storage tank includes: a temperature controlling liquid cooling bath with a storage tank cooling means positioned therein; and a temperature controlling liquid storage bath for storing the temperature controlling liquid cooled in, and provided by, the temperature controlling liquid cooling bath, wherein the temperature controlling liquid storage bath includes a dispensation opening for dispensing the temperature controlling liquid using the dispensing apparatus.

8. The method of stabilizing a constant-temperature bath of an automatic analysis apparatus according to claim 7, wherein in the dispensing step, the cooled temperature controlling liquid is dispensed into the empty reaction container at the timing of dispensing a first reagent.

9. The method of stabilizing a constant-temperature bath of an automatic analysis apparatus according to claim 7, wherein in the dispensing step, a dispensing amount of the temperature controlling liquid is defined as an average amount of the reagent and the specimen dispensed in each analysis item.

* * * * *